United States Patent [19]
Bendele et al.

[11] Patent Number: 6,143,578
[45] Date of Patent: Nov. 7, 2000

[54] METHOD AND APPARATUS FOR WASH, RESUSPENSION, RECOLLECTION AND LOCALIZATION OF MAGNETIZABLE PARTICLES IN ASSAYS USING MAGNETIC SEPARATION TECHNOLOGY

[75] Inventors: Teresa M. Bendele, Brunswick; Linda A. Harrison, Huron; David J. Howard, Oberlin; Lori K. Knotts, Medina; Michael L. Malek, North Olmsted; Todd A. Veverka, Bay Village, all of Ohio

[73] Assignee: Bayer Corporation, Tarrytown, N.Y.

[21] Appl. No.: 09/174,494

[22] Filed: Oct. 16, 1998

Related U.S. Application Data

[63] Continuation-in-part of application No. 08/644,909, May 10, 1996, Pat. No. 5,888,835.

[51] Int. Cl.$^7$ .................. G01N 33/553; G01N 35/02; B03C 1/00; B01D 35/06; C12M 1/00
[52] U.S. Cl. .................. 436/526; 436/47; 436/807; 436/809; 209/214; 210/222; 210/695; 435/287.1; 435/287.2; 435/287.3; 422/65; 422/68.1; 422/101; 422/102
[58] Field of Search .................. 436/526, 47, 807, 436/809; 209/214; 210/222, 695; 435/287.1, 287.2, 287.3; 422/65, 68.1, 101, 102

[56] References Cited

U.S. PATENT DOCUMENTS

| | | | |
|---|---|---|---|
| 4,265,855 | 5/1981 | Mandle et al. | 422/65 |
| 4,628,037 | 12/1986 | Chagnon et al. | 436/526 |
| 4,661,408 | 4/1987 | Lau et al. | 428/405 |
| 4,698,302 | 10/1987 | Whitehead et al. | 435/94 |
| 4,745,077 | 5/1988 | Holian et al. | 436/526 |
| 4,785,407 | 11/1988 | Sakagami | 364/497 |
| 5,104,808 | 4/1992 | Laska et al. | 436/48 |
| 5,108,933 | 4/1992 | Liberti et al. | 436/501 |
| 5,128,103 | 7/1992 | Wang et al. | 422/64 |
| 5,147,529 | 9/1992 | Lee et al. | 210/695 |
| 5,183,638 | 2/1993 | Wakatake | 422/64 |
| 5,186,827 | 2/1993 | Liberti et al. | 210/222 |
| 5,200,084 | 4/1993 | Liberti et al. | 210/695 |
| 5,232,665 | 8/1993 | Burkovich et al. | 422/65 |
| 5,256,532 | 10/1993 | Melnicoff et al. | 435/5 |

(List continued on next page.)

FOREIGN PATENT DOCUMENTS

| | | |
|---|---|---|
| 0358948 | 3/1990 | European Pat. Off. . |
| 0371265 | 6/1990 | European Pat. Off. . |
| 0410645 | 1/1991 | European Pat. Off. . |
| 0502638 A2 | 9/1992 | European Pat. Off. . |
| 0589636 | 3/1994 | European Pat. Off. . |
| 589636 A1 | 3/1994 | European Pat. Off. . |
| 0806665 A1 | 11/1997 | European Pat. Off. . |
| 91/09308 | 6/1991 | WIPO . |
| 91/16979 | 11/1991 | WIPO . |
| 93/13400 | 7/1993 | WIPO . |

OTHER PUBLICATIONS

Advanced Magnetics Inc. (Jul. 1984) "Instructions and Precautions for Handling Biomag".

*Primary Examiner*—Christopher L. Chin
*Assistant Examiner*—Pensee Do
*Attorney, Agent, or Firm*—Weingarten, Schurgin, Gagnebin & Hayes LLP

[57] ABSTRACT

Method and apparatus for enabling resuspension wash and magnetic localization of sample components bound to particles with magnetic properties in reaction vessels during separation and wash for enhanced chemiluminescent signal generation in biomedical assays. The assays involve moving reaction vessels past magnets that partially localize the particles prior to passing a reduced strength magnet where washing occurs, with or without resuspension, after separating out the unbound particles and liquid. The band of particles is subsequently resuspended in acid for chemiluminescent purposes. A variety of magnet configurations are employed to realize the reduced strength magnet. Reduced strength magnets adjacent the full width magnets prevent the band of magnetic particles from becoming split. The localized particles enable more efficient resuspension by reagent.

5 Claims, 6 Drawing Sheets

U.S. PATENT DOCUMENTS

| | | | |
|---|---|---|---|
| 5,278,080 | 1/1994 | Midgley et al. | 436/500 |
| 5,283,079 | 2/1994 | Wang et al. | 427/2 |
| 5,374,531 | 12/1994 | Jensen | 435/7.24 |
| 5,395,688 | 3/1995 | Wang et al. | 428/327 |
| 5,466,574 | 11/1995 | Liberti et al. | 435/5 |
| 5,491,068 | 2/1996 | Benjamin et al. | 435/7.32 |
| 5,741,708 | 4/1998 | Carey et al. | 436/49 |

FIG.5A
WITHOUT RESUSPENSION WASH

FIG. 5B
WITH RESUSPENSION WASH

FIG.6

METHOD AND APPARATUS FOR WASH, RESUSPENSION, RECOLLECTION AND LOCALIZATION OF MAGNETIZABLE PARTICLES IN ASSAYS USING MAGNETIC SEPARATION TECHNOLOGY

RELATED APPLICATIONS

This application is a continuation-in-part of U.S. patent application Ser. No. 08/644,909, filed May 10, 1996, issued as U.S. Pat. No. 5,888,835 on Mar. 30, 1999.

FIELD OF THE INVENTION

The invention generally relates to the field of biomedical assays employing magnetic separation techniques, and specifically to a method and apparatus for focusing or localizing magnetizable particles during separation and wash in such assays.

BACKGROUND OF THE INVENTION

Heterogeneous immunoassays typically require the separation of sought-for components bound to component-selective particles from unbound or free components of the assay. To increase the efficiency of this separation, many assays wash the solid phase (the bound component) of the assay after the initial separation (the removal or aspiration of the liquid phase). Some chemiluminescent immunoassays use magnetic separation to remove the unbound assay components from the reaction vessel prior to addition of a reagent used in producing chemiluminescence or the detectable signal indicative of the amount of bound component present. This is accomplished by using magnetizable particles including, but not restricted to, paramagnetic particles, superparamagnetic particles, ferromagnetic particles and ferrimagnetic particles. Tested-for assay components are bound to component-specific sites on magnetizable particles during the course of the assay. The associated magnetizable particles are attracted to magnets for retention in the reaction vessel while the liquid phase, containing unbound components, is aspirated from the reaction vessel.

Washing of the solid phase after the initial separation is accomplished by dispensing and then aspirating a wash solution, such as de-ionized water or a wash buffer, while the magnetizable particles are attracted to the magnet.

Greater efficiency in washing is accomplished by moving the reaction vessels along a magnet array having a gap in the array structure proximate a wash position, allowing the magnetizable particles to resuspend during the dispense of the wash solution. This is known as resuspension wash. Subsequent positions in the array include magnets, allowing the magnetizable particles to recollect prior to aspiration of the wash solution and introduction of reagent beyond the end of the magnet array.

Prior art wash block configurations have employed iron-based or non-iron-based inserts in the gap of the magnet array at the wash position. Rather than simply removing a magnet from the resuspension position, the insert is intended to maintain the accumulation of magnetic particles in the absence of resuspension wash, and to orient these particles for thorough resuspension if resuspension wash is employed. In addition, the insert prevents a reaction vessel from becoming misaligned and jammed in the magnet array. While functioning adequately for assays which employ resuspension wash, it is evident that the provision of such inserts in place of a magnet at the wash position adversely effects assays which do not use the resuspension in washing but which proceed through the wash position without resuspension. With a non-iron-based insert such as of aluminum or ceramic, a single band of magnetizable particles which is normally formed along the interior of the reaction vessel as it passes the magnet array, during the initial separation, is split into two smaller bands on either side of the reaction vessel due to attraction by the magnets on either side of the insert at the resuspension and wash position. This is due to the minimal effect by the insert on the magnetic flux patterns. Since reagent is introduced into the reaction vessel in a stream directed toward where the magnetizable particles collected before splitting, the split in the banding of the magnetizable particles results in the stream missing the main concentration of magnetizable particles. Poor resuspension of the magnetizable particles during resuspension wash and upon addition of an acid reagent used to condition the bound component reagent in the generation of a chemiluminescent signal results.

Similarly, the use of an iron-based insert such as of steel may result in split-banding of the magnetic particles, but may further introduce a band of particles in the middle of the cuvette wall adjacent the insert. This is due to the tendency of an iron-based insert to shunt magnetic fields. While the formation of a band or pellet of particles in the middle of the cuvette wall is desired, the reproducibility of this response across varying assays for a single iron-based insert configuration is unlikely. This is due to the varying characteristics of the assays, including concentration of surfactants and the particle masses.

Other prior art approaches for facilitating resuspension wash have employed inserts of reduced width with the intention that magnetic fields extending from the adjacent magnets will hold the magnetic particles in position. However, this approach has also resulted in the split-banding of the particles.

Therefore, the prior art fails to provide a wash region which enables the efficient washing of magnetizable particles during the wash phase of a magnetic separation assay without adversely effecting assays not employing resuspension wash.

SUMMARY OF THE INVENTION

It is an object of the present invention to provide methods and apparatus for focusing or localizing magnetizable particles during separation and wash for enhanced signal generation in assays which use magnetic separation technology.

It is a further object of the present invention to provide a wash region enabling enhanced suspension of solid phase components for a sample, regardless of whether it undergoes resuspension wash.

These objects are achieved by employing an insert of soft magnetic material in place of separation magnets at a wash position in the array, wherein the insert has a width greater than the width of a reaction vessel passing thereby. Further, the magnets of the array both up and downstream of the wash position terminate at locations intermediate to the reaction vessel for enhanced focusing of magnetizable particles in the path of a reagent stream, resulting in improved resuspension of the magnetizable particles by the reagent. Therefore, resuspension wash efficiency is enhanced, and magnetizable particle focusing is increased, leading to a more efficient magnetizable particle resuspension for the signal generation portion of the assay.

At the end of the magnet array, a focusing magnet having a face dimension less than a vessel width is employed in the array to more completely localize the magnetizable particles prior to being in the path of an injected acid stream employed to initiate the reaction leading to chemiluminescence.

For assays not employing resuspension wash, the provision of the soft magnetic insert results in avoidance of split banding of the magnetizable particles, while magnetizable particle focusing results in improved chemiluminescent reaction.

For assays employing resuspension wash, the soft magnetic insert enables resuspension wash while avoiding premature collection and splitting of magnetizable particles due to the influence of magnets adjacent to the wash position. As with assays not employing resuspension wash, magnetizable particle focusing results in improved chemiluminescent reaction.

It is a further object of the present invention to provide a wash region which enables the accurate and predictable collection of magnetizable particles, whether or not resuspension wash is performed at that region.

This object is achieved, in an alternative embodiment, through the provision of a magnet of reduced strength, relative to the other magnets in the array, at the wash position. For instance, in a preferred embodiment, the reduced strength magnet provides a magnetic field at the respective reaction vessel position one-half that as provided by the other magnets. This reduced strength magnet acts as a replacement for the soft magnetic insert previously mentioned, which, on its own, provides no magnetic field. Additionally, the magnets of the array which are disposed at reaction vessel positions before and after the wash position are not trimmed, but instead extend across the full extent of the respective reaction vessel position. At the last reaction vessel position in the array, the respective magnet is disposed on a side of the reaction vessel opposite that of all previous magnets in order to avoid the dense packing in collected particles which sometimes results in incomplete resuspension in the stream of final reagent. A further feature of this alternative embodiment includes lowering the focal point of the magnetic field, generated by magnets of the array, at a reaction vessel position immediately following the reaction vessel position having the reduced strength magnet proximate thereto.

BRIEF DESCRIPTION OF THE DRAWINGS

This invention is pointed out with particularity in the appended claims. The above and further advantages may be more fully understood by referring to the following description and accompanying drawings of which:

DETAILED DESCRIPTION

To increase the efficiency of the separation of bound components from free components in immunoassays, many assays wash the solid phase (bound component) of the assay after the initial separation (removal of the liquid phase and unbound component). The present invention operates in the context of a chemiluminescent immunoassay of known type which uses magnetic separation to remove unbound assay components from a reaction vessel such as a cuvette.

The presently disclosed method and apparatus enables a resuspension wash of magnetizable particles with improved wash efficiency and focuses magnetizable particles from a band to a small region or dot, enabling a more efficient resuspension of magnetizable particles for a signal generation portion of the assay.

In all of the following discussions, it is assumed that the reaction vessels progress from the left-hand side of the illustrations to the right-hand side past a fixed magnet array at regularly timed intervals, although continuous motion is not excluded. Means for imparting lateral translation of the reaction vessels is described subsequently with regard to FIG. 2. In an exemplary embodiment, such interval is approximately 15 seconds. Additionally, throughout this description, aspiration and dispense functions are executed via means known in the art without full details being shown.

Figure 1A:
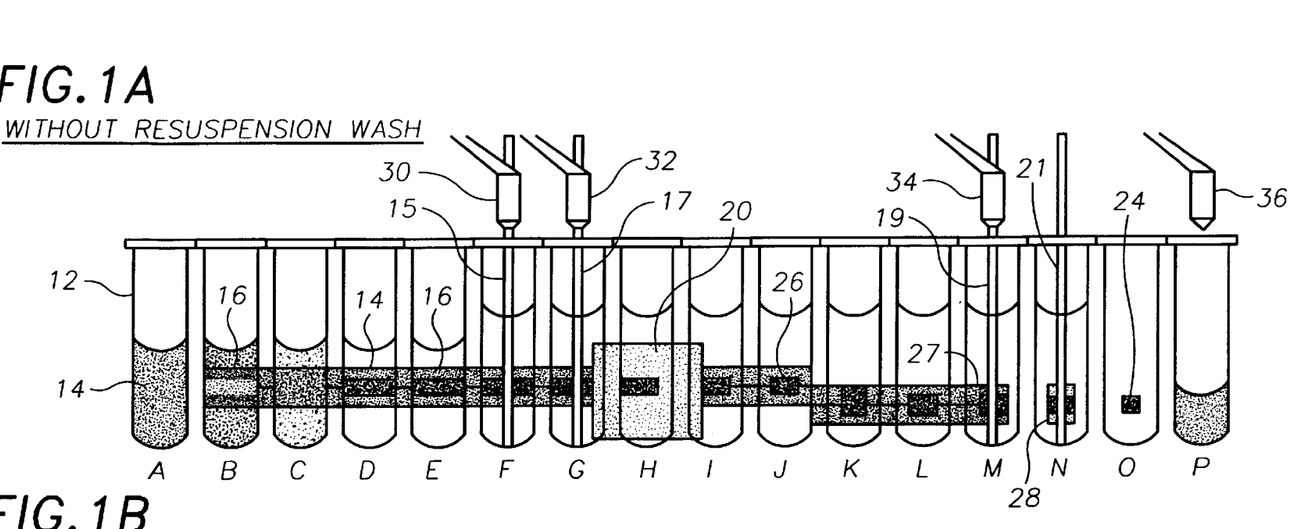
FIG. 1A is an elevation view of a magnet array and a sequence of reaction vessels passing therethrough according to the present invention.
Figure 1B:
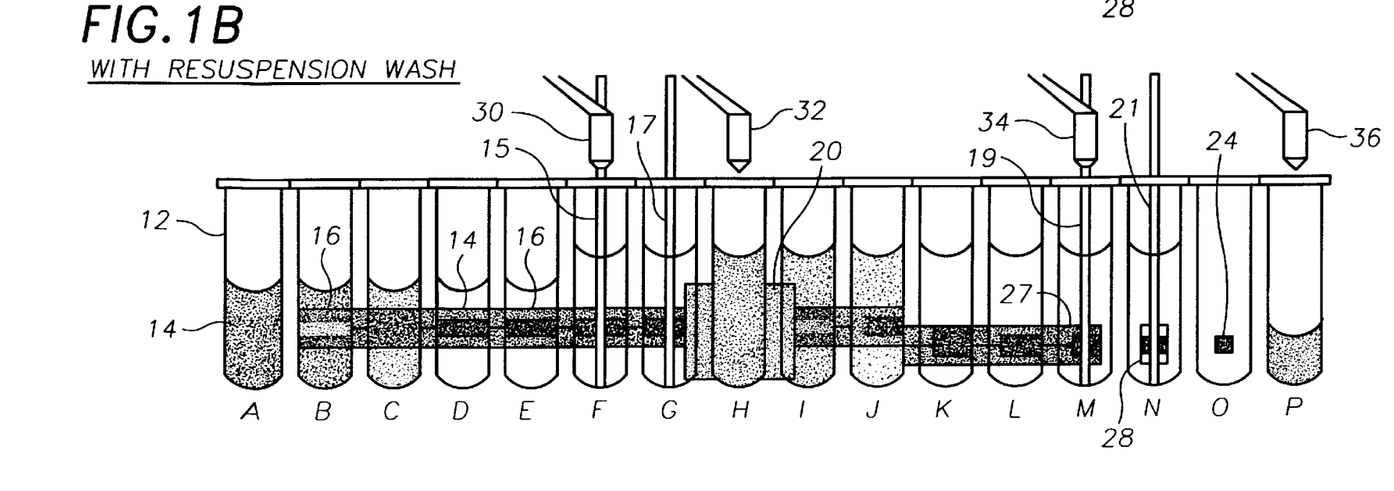
FIG. 1B is an elevation view of the magnet array of FIG. 1A in which resuspension wash is performed.

The magnet array of FIGS. 1A and 1B includes a succession of reaction vessels such as cuvettes 12, each containing assay components and magnetizable particles 14 which are initially in a freely distributed state within the respective cuvette 12. The concentration of solid phase (bound component) of the assay remaining in free suspension in the cuvette at position B is less than that of the first cuvette 12 in position A due to the initial collection of solid phase proximate magnets of the array 16 at position B. In the cuvette 12 of position C, this effect is more evident. By the time a cuvette has progressed to position D, the majority of the solid phase 14 has collected proximate respective magnets of the array 16.

References to "magnets" adjacent a respective position are understood to refer to a pair of adjacent magnets of oppositely oriented polarity, one above the other, proximate the respective cuvette position. A band of magnetizable particles 14 forms along the junction of these two magnets, where the magnetic gradient is at a maximum.

Non-resuspension washes are provided at positions F, G, and M in the illustrative embodiment of FIG. 1A, and at positions F and M in the embodiment of FIG. 1B. At these positions, liquid phase is aspirated from the cuvette 12 via tubes (15, 17, 19 in FIG. 1A and 15, 19 in FIG. 1B) and wash solution is reintroduced via nozzles (30, 32, 34 in FIG. 1A and 30, 34 in FIG. 1B). The nozzles are positioned in front of respective tubes in the view of FIGS. 1A and 1B. In particular, the nozzles are angled toward the front of the respective cuvette 12 (out of the page in FIGS. 1A and 1B) to avoid disturbing the pellet of solid phase 14 collected at the respective magnets of the array 16.

The tube 21 at position N of FIGS. 1A and 1B is employed to aspirate liquid phase from the respective cuvette 12 prior to the introduction, at position P, of reagent via nozzle 36, the reagent facilitating a subsequent chemiluminescent reaction within a luminometer. In contrast to the non-resuspension wash nozzles (30, 32, 34 in FIG. 1A and 30, 34 in FIG. 1B), the reagent dispensing nozzles 36 are angled toward the pellet of solid phase 14 in order to thoroughly disperse it.

In prior art magnet arrays, a portion of the liquid phase may remain trapped within the solid phase 14 prior to introduction of the reagent at position P, even after repeated non-resuspension washes, such as at positions F, G, and M in FIG. 1A and positions F and M in FIG. 1B. This trapped liquid phase limits the accuracy of the assay.

At position K of FIG. 1A, the magnets of the array 16 proximate the cuvettes 12 are disposed at a lower position. This provides the solid phase pellet 14 with time to recollect at the lower position prior to the introduction of assay reagent at position P. Thus, when reagent is directed at the pellet 14 in position P by the nozzle 36, the solid phase 14 will be centrally located in the reaction vessel 12 when the acid is applied at position P. However, such repositioning of the pellet does not necessarily enhance the ability of the nonresuspension washes to rid the solid phase 14 of trapped liquid phase.

In FIG. 1A, a resuspension wash is not employed, and as such the focused, or localized, solid phase remains proximate respective magnets 16 as the cuvette 12 progresses through the wash block.

In contrast, the magnet array of FIG. 1B does employ a resuspension wash. Resuspension washing of the solid phase involves the aspiration of the liquid phase containing the unbound components of the assay from the cuvette 12 at position G via the tube 17 while the bound components are held in place by respective magnets in the array 16. This is followed by reintroduction of wash solution into the cuvette 12 at position H by a dispense nozzle 32 angled at the solid phase pellet 14 collected at the back of the cuvette 12 proximate the magnets 16.

At position H, magnets of the array 16 have been replaced by a soft magnetic insert 20. By dispensing wash solution onto the magnetizable particles via the nozzle 32 in the absence of magnets in the array 16, the magnetizable particles are resuspended, exposing more surface area, and freeing liquid phase trapped during initial magnetizable particle collection. After the solid phase has been resuspended, it is recollected by a subsequent series of magnets in the array 16 at positions I et seq. prior to aspiration of the wash solution and introduction of the acid reagent at position P. Other wash stages, in addition to those illustrated, are possible.

The wash block of FIGS. 1A and 1B is provided with a large gap in the magnet array at position H, thus enhancing resuspension wash. Prior art magnet arrays employed narrower gaps, resulting in split bands of magnetizable particles due to the attractive forces of array magnets on either side of the narrow gap.

The present invention avoids the splitting of the solid phase material into bands at opposite sides of the cuvette 12, in part, by providing a focusing of the solid phase 14 into a smaller band or dot 24. The gap at the resuspension wash position is filled with an insert 20 made of a soft magnetic material such as low carbon steel. Further, the magnets of the array 16 at positions G and I on either side of the resuspension wash position, position H, are trimmed such that the gap in the array of magnets 16 and the insert 20 extend proximate a region of the reaction vessels 12 previously occupied by the solid phase band 14 adjacent to the resuspension wash position.

As a result, magnetizable particles linearly banded by the magnets in the previous positions, but which are no longer directly aligned with magnets of the array 16, migrate along the reaction vessel 12 walls towards portions of the reaction vessel interior proximate the trimmed magnets 16. For instance, in position G, the magnets 16 are trimmed on the right-hand side. Magnetizable particles formerly aligned in the trimmed region now migrate to the center of the vessel 12, over the trimmed magnets 16.

The magnetizable particle banding pattern in the reaction vessel at the resuspension wash position, position H, remains unchanged in the absence of resuspension wash (FIG. 1A). With resuspension wash (FIG. 1B), the large soft magnetic insert 20 enables the complete resuspension of the solid phase 14 free of influence of magnets at positions G and I. Also, the provision of magnets trimmed on a left-hand side at position I downstream of the resuspension wash position, position H, further serves to avoid influencing the magnetizable particles during the resuspension wash in FIG. 1B.

The array 16 magnets at position I, downstream of the resuspension wash position, position H, and the soft magnetic insert 20, is also trimmed on its left-hand side in FIG. 1A. This serves to focus the solid phase 14 downstream of the resuspension wash position, position H. The magnetizable particles on the left side of the reaction vessel 12 are no longer directly aligned with magnets 16 at position I. Rather, they migrate toward the right, into the center of the vessel 12. The net effect is a conversion of the magnetizable particles from a wide band 14 to a more compact, centrally located band 26.

For the embodiment of FIG. 1A, the single magnetizable particle band at position H does not split into two bands as in the prior art because the soft magnetic insert 20 acts to short out, or minimize, the magnitude of the field gradient in the resuspension wash position, position H, and because trimming the magnets of the array 16 at positions G and I reduces the reach of the fields, from the same, into the resuspension position H.

At position M, trimmed magnets 27 are provided to further narrow the band of collected magnetizable particles. In a further embodiment, even smaller magnets 28, focusing magnets, are employed at position N to focus the magnetizable particles into yet a smaller area, thus providing a smaller target of solid phase 24 at position P for more efficient resuspension upon dispense of reagent. Smaller, focusing magnets 28 are not used in a preferred embodiment for the initial collection of the solid phase because, amongst other things, the larger the magnet surface area, the faster the collection of the magnetizable particles.

In an alternative embodiment, all of the magnets in the array 16 along the length of the wash block are provided as focusing magnets 28, though the resuspension wash position, position H, would continue to be provided with a gap such as that provided by the soft magnetic block 20 of FIGS. 1A and 1B. However, such an embodiment would require more time for each reaction vessel 12 to be proximate the magnets 28 in the array to provide an equivalent degree of capture capability due to the smaller size of the magnets in such an embodiment.

In yet another embodiment of the present invention, it is possible to enable further focusing of the magnetizable particles by employing another gap in the magnet array 16 prior to the focusing magnets 28 at position N. For instance, such a gap could be employed at position L. Here, the magnetizable particles 14 have already been gathered at an interior wall of the reaction vessel 12. A gap at position L would allow the magnetizable particles to become released from the interior wall, though they would generally remain localized. Thus, reattraction by subsequent focusing magnets 38 would not take an excessive amount of time.

Figure 2:
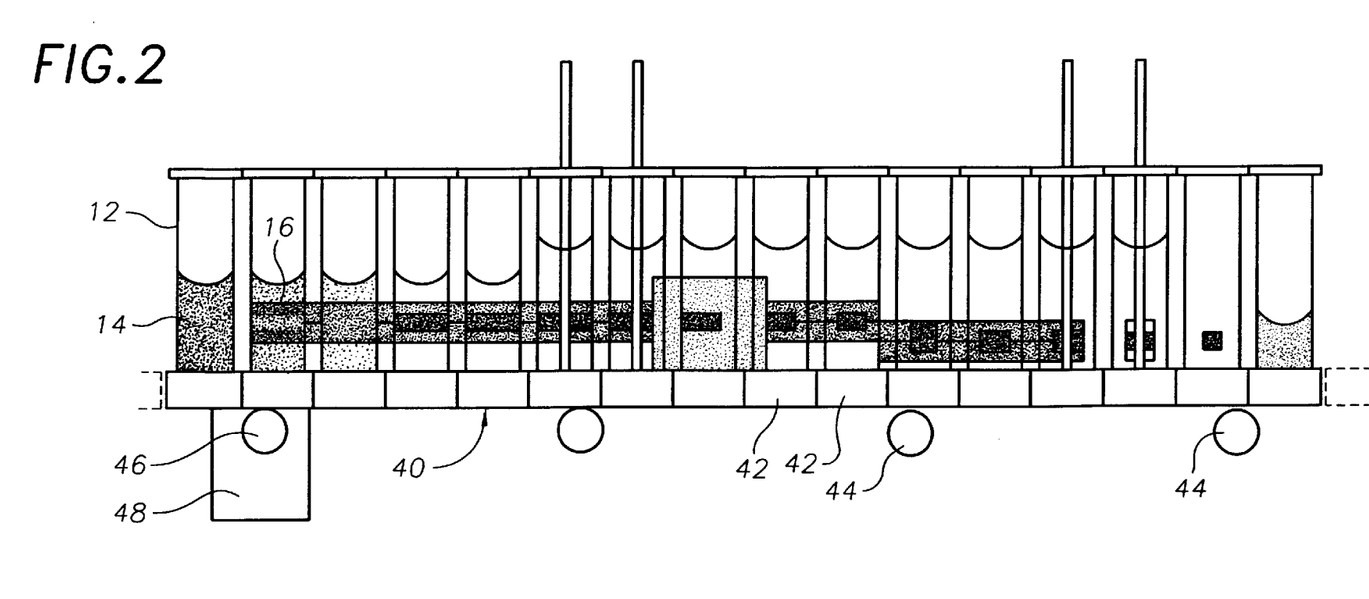
FIG. 2 is an elevation view of the magnet array of FIG. 1A illustrating a reaction vessel transport mechanism.

Illustratively, in a first embodiment illustrated in FIG. 2, the reaction vessels 12 containing the suspended solid phase 14 are laterally translated along the magnet array 16 by a linked conveyor belt 40 comprised of a sequence of reaction vessel receptacles 42. A sequence of freely rotatable rollers 44 are employed to provide support for the conveyor belt 40. At least one such roller 46 is mechanically connected to a motor 48, wherein the motor 48 rotates this roller 46, which in turn causes the conveyor belt 40 and the reaction vessels 12 disposed therein to translate relative to the magnet array 16.

Figure 3:
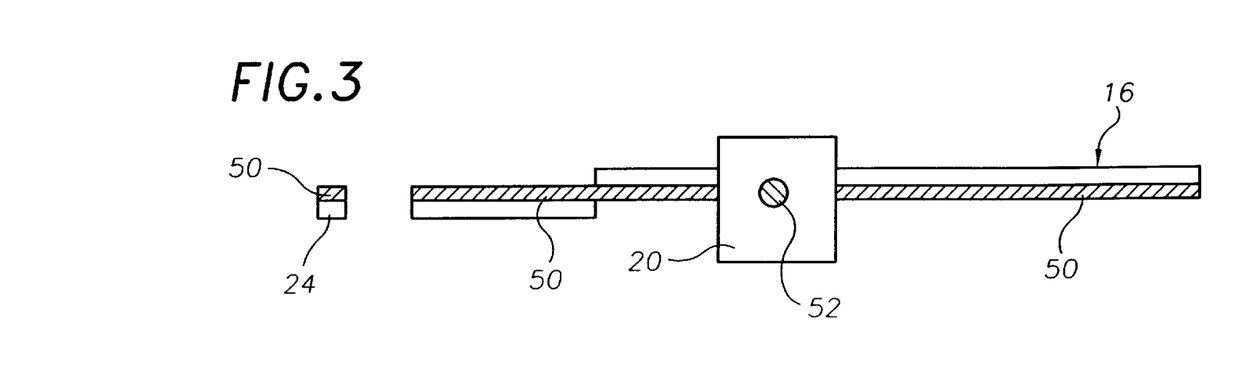
FIG. 3 is a rear elevation view of the magnet array of FIG. 1A illustrating a magnet array support structure.

The rear view of the magnet array in FIG. 3 illustrates a first embodiment of a magnet array 16 support structure 50. The magnet array 16 of FIG. 3 is a reverse view of the magnet array 16 of FIGS. 1A and 1B. The magnets of the array are backed by a conductive material such as high-iron, low-carbon steel to focus the magnetic field toward the reaction vessels 12. The support structure 50, which attaches to the magnet backing material, is preferably provided from a magnetically non-reactive material such as aluminum or one of its alloys to avoid unwanted disturbances in the magnetic field established within the reaction vessels. The magnets of the array 16 and the backing material are fastened to the support structure 50 in a variety of ways, including via the use of adhesive or mechanical fasteners. The support structure 50 is itself suspended by being mechanically attached to a wall of an enclosure (not illustrated), either by adhesive, mechanical fasteners, or some combination thereof.

In the illustrated embodiment of the support structure in FIG. 3, the element is segmented into three portions: an initial portion to the right of FIG. 3, a central portion, and a small final portion on the left. The latter provides support for the focusing magnets 24. In an alternative embodiment, the central portion and the final portion are combined, such that the support structure is formed of two portions.

FIG. 3 also illustrates a rear view of the soft magnetic insert 20. Disposed in a central location thereof is a cross-section of a mechanical fastener 52 such as a screw employed in securing the insert 20 to a wall of the enclosure. In alternative embodiments, the soft magnetic insert is supported by a respective support element such as a stanchion or by an extension of the array magnet support element 50. In the latter alternative, the support element 50 would then be one continuous element, if the final portion and the central portion are continuous, or two elements if the focusing magnets 24 is supported independently.

Figure 4A:
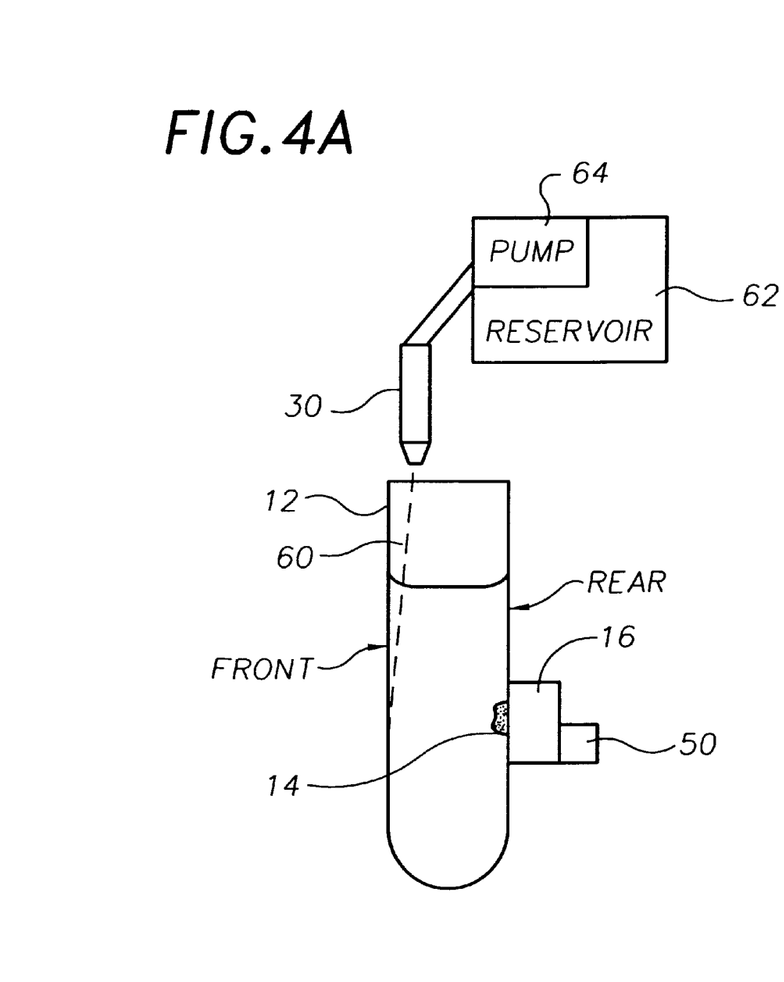
FIG. 4A is a side elevation view of a non-resuspension wash nozzle oriented proximate a reaction vessel for use in the magnet array of FIG. 1A.
Figure 4B:
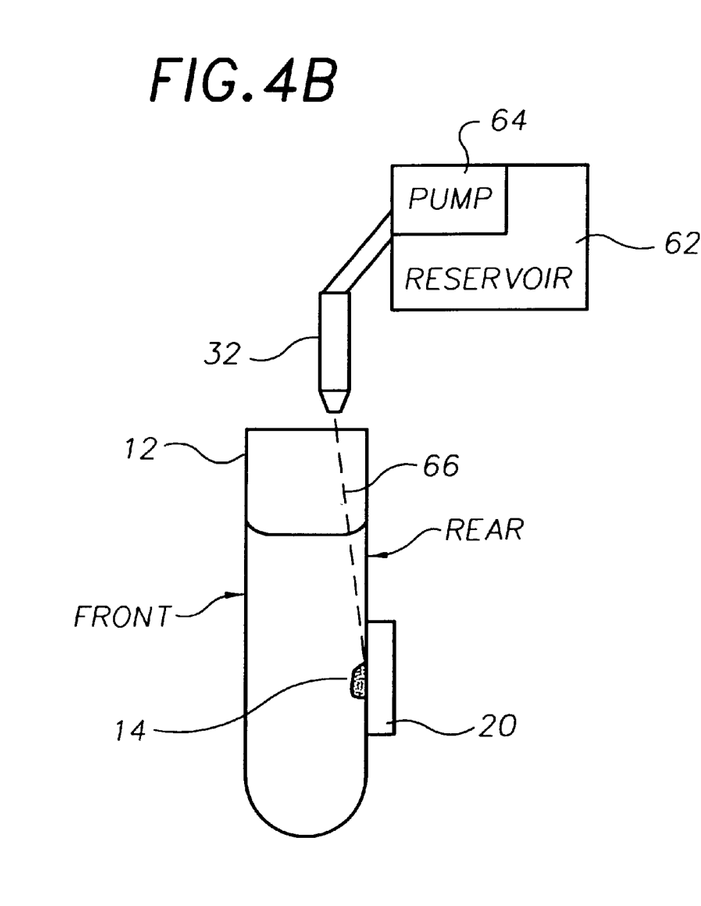
FIG. 4B is a side elevation view of a resuspension wash nozzle oriented proximate a reaction vessel for use in the magnet array of FIG. 1B.

The orientation of wash solution nozzles as employed along the magnet array 16 of the foregoing is illustrated in FIGS. 4A and 4B. In particular, a nozzle 30 such as that used for reintroduction of wash solution at position F in FIGS. 1A or 1B is shown in cross-section in FIG. 4A. Solid phase 14 has collected proximate the magnet array 16 (supported by the support element 50) at the rear of the reaction vessel 12. The nozzle 30 is oriented with respect to the reaction vessel 12 to provide a stream 60 of wash solution from a wash solution reservoir 62 via a pump 64 to a front, interior surface of the reaction vessel 12. This avoids disturbing the solid phase collected at the rear of the vessel 12.

In FIG. 4B, the orientation of a nozzle 32 such as that used for resuspension wash at position H in FIG. 1B is illustrated in FIG. 4B. A stream 66 of wash solution from the reservoir 62 via the pump 64 is directed at the solid phase previously collected proximate magnets in the array 16, but now adjacent to the soft magnetic insert 20. The solid phase is therefore not retained by magnets, and is easily washed back into suspension by the stream 66 of wash solution from the nozzle 32.

Having described preferred embodiments of the invention, it will be apparent to those skilled in the art that other embodiments incorporating the concepts may be used. For instance, though the present invention has been described in the context of a chemiluminescent immunoassay, it can be applied to other assay environments in which the separation of bound and unbound components by magnetic separation is required. Further, the exact number of positions in which magnetizable particles are exposed to magnets 16 depends upon the exact nature of the desired separation, the configuration of the magnets 16, the characteristics of the magnetizable particles and the associated bound component, etc.

Nozzle 32 has been shown in two locations in FIGS. 1A and 1B, specifically position H in FIG. 1A and position I in FIG. 1B. While provided as one nozzle with a like reference identifier in both figures, each embodiment of FIG. 1A and 1B could be provided with a nozzle at position G for non-resuspension wash, and another nozzle at position H for use in an embodiment employing resuspension wash. Thus, the same array configuration could be used for assays both employing and not employing resuspension wash.

In addition to the illustrated embodiment of FIG. 2, other means for translating the conveyor belt are envisioned, such as a friction drive disposed on either side of the conveyor at one or more positions.

In yet another embodiment of the present invention, the reaction vessels 12 are translated along the magnet array 16 by way of a sequence of respective reaction vessel yokes (not illustrated) connected to the respective reaction vessel near the top of the vessel.

The arrangement of elements in FIGS. 4A and 4B is a generalized illustration of the relationship between the elements, and is not intended to represent a preferred layout.

For instance, the nozzle 30, 32 in FIGS. 4A and 4B can also be located at the same relative position above a respective reaction vessel 12, but angled in opposite directions to properly direct the respective stream 60, 66. Further, the pump and reservoir can be provided in a variety of ways, as known to one skilled in the art.

The embodiments described in the foregoing are best suited to particles and particle mixtures that relocate easily within and along the wall of a reaction vessel in response to changes in magnetic fields in the vicinity of the reaction vessel. By "particle mixtures," it is meant mixtures including magnetic particles, the sample, primary reagents, ancillary reagents and wash solutions. Such easily relocatable mixtures form consistently shaped and accurately positioned pellets. Factors which contribute to the responsiveness of mixtures to applied magnetic fields include the size of the magnetic particles, the "stickiness" of substances in the reaction mixture, the inclusion of "slippery" surfactants in the reaction mixture, etc.

Assay mixtures which do not relocate easily or consistently in response to moving magnetic fields tend to form pellets of variable shapes in unpredictable locations, particularly at positions N, 0 and P of FIGS. 1A and 1B. This inconsistency diminishes the benefit of shaping and positioning the particle mass, since it introduces variability in the resuspension step where the final reagent is introduced. In addition, some assay mixtures tend to pack the aggregate of particles more densely as the magnetic forces shape and position them, thus frustrating efforts taken to remove unbound label which might otherwise improperly effect the desired reaction.

In general, it is desirable to minimize the number of different wash steps in the separation and wash process; additional process steps have the potential for introducing variability. However, in certain assays, additional wash steps are necessary to localize the magnetic particles into a band on the side wall of a reaction vessel. Some assays benefit significantly from a resuspension wash step. Resuspension wash is used to wash out any unbound label that may be trapped in the particle aggregate which would otherwise contribute a non-specific signal to the true signal at the assay read step. Therefore, as provided in the previous embodiment, a further embodiment provides the ability to selectively employ a resuspension wash, but with an emphasis placed on minimizing unnecessary manipulation of the particle aggregate.

Figure 5A:
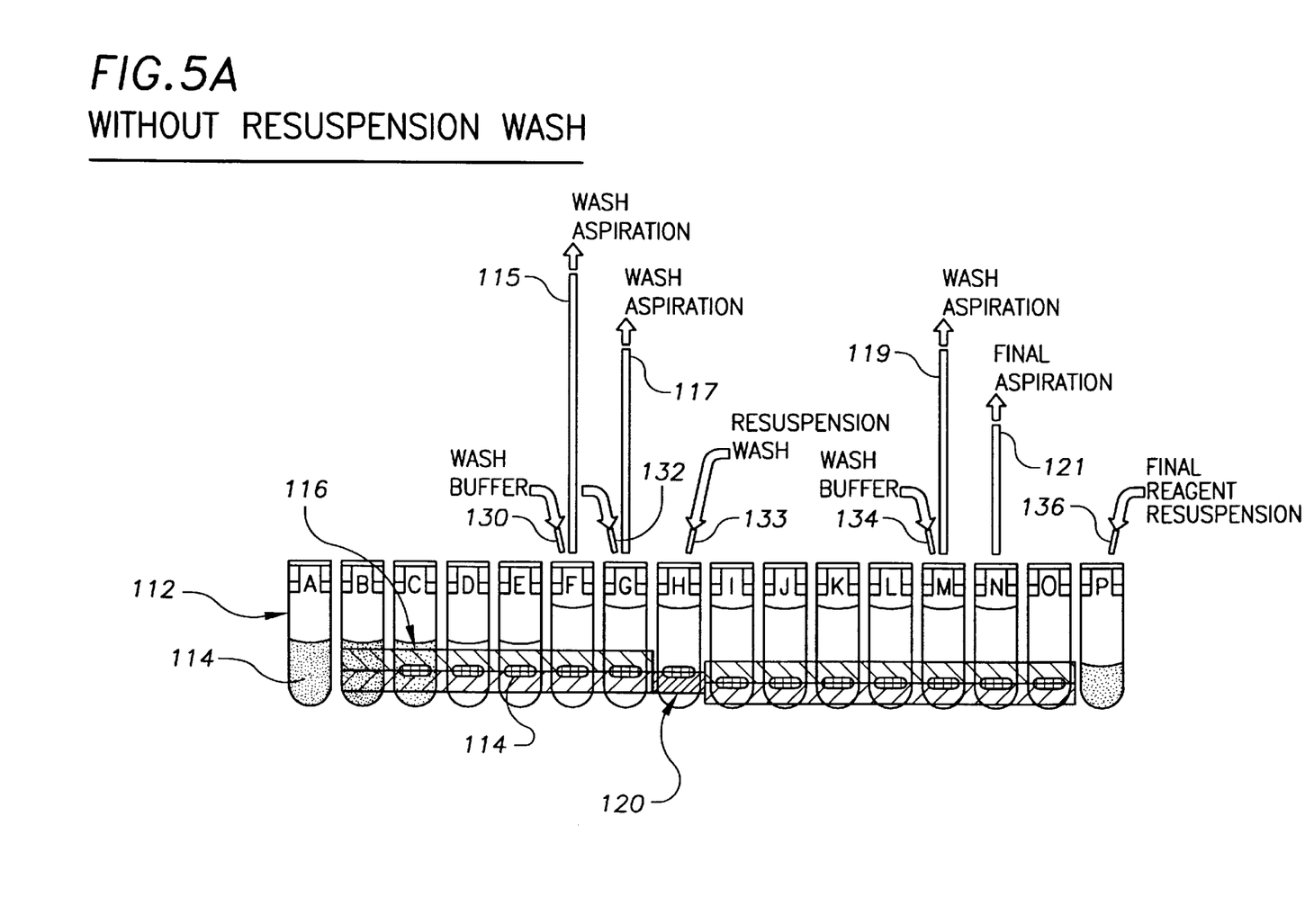
FIG. 5A is an elevation view of a magnet array and a sequence of reaction vessels passing therethrough according to a further embodiment of the present invention.

FIG. 5A is an illustration of a system having a continuous magnet array proximate a series of consecutive reaction vessel positions. The array is comprised of vertically oriented pairs of magnets 116, one above the other, arranged such that the magnetic gradient generated by the magnets at each reaction vessel position has a horizontal maximum proximate the intersection of the two magnets. As in the previously described embodiment, each reaction vessel, or cuvette, 112 contains assay components and magnetizable particles 114 which are initially in a freely distributed state within the respective cuvette 112 (for instance, at position A). The concentration of unbound solid phase decreases as each cuvette traverses the magnet array (from left to right in FIGS. 5A and 5B).

Figure 5B:
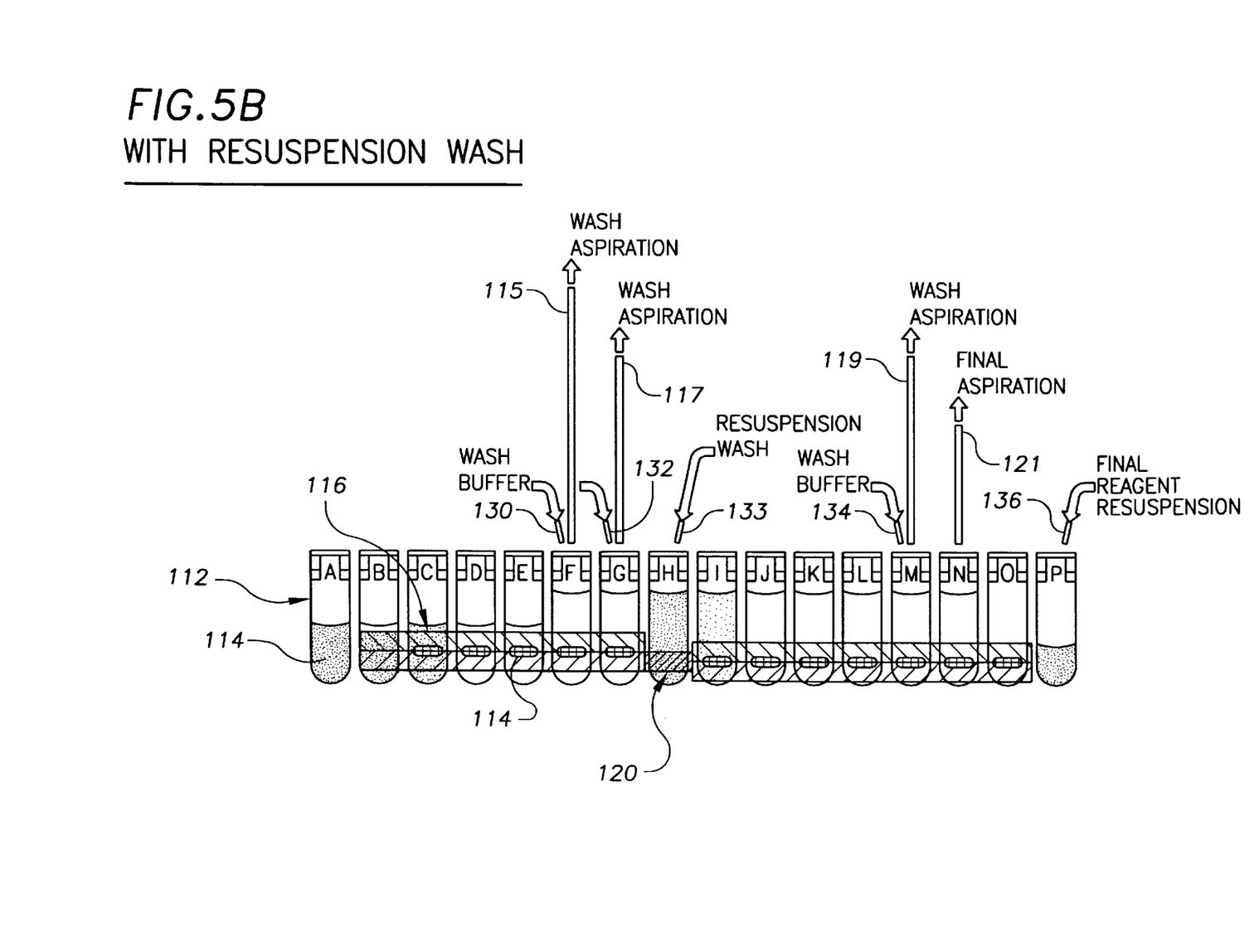
FIG. 5B is an elevation view of the magnet array of FIG. 5A in which resuspension wash is performed.

For ease of reference, reaction vessel positions B through G are referred to as an initial separation stage, at which the solid phase is initially collected against the interior wall of the cuvette, proximate the respective magnets 116. One or more non-resuspension washes (discussed subsequently) may be provided within the initial separation stage. Position H is referred to as a resuspension wash position, at which a resuspension wash may occur according to the needs of each assay. Positions I through M are referred to as a subsequent separation stage, even though in the case of FIG. 5A, there is no resuspension wash and so the separation begun in the initial separation stage is merely continued. In the case of FIG. 5B, however, the subsequent separation stage is utilized for the purpose of separating the magnetic particles into a pellet against the cuvette interior wall most proximate the magnet array. One or more non-resuspension washes may occur within the subsequent separation stage (discussed subsequently). Position N is referred to as a final aspiration stage, where liquid phase is removed from the cuvette prior to the final reagent resuspension. Position O is an optional rest stage. Position P is referred to as a final resuspension stage, where a final reagent is introduced into the cuvette at such an angle that the previously collected pellet 114 is washed off the cuvette wall and is freely suspended in the reagent solution.

As in FIG. 1A, optional non-resuspension wash positions are provided at positions F, G and M. Here, liquid phase is aspirated from the cuvette 112 via tubes 115, 117, 119, and wash solution is introduced via nozzles 130, 132, 134. While these nozzles are labeled "WASH BUFFER" in the figures, it is understood that any wash solution desired may be dispensed from the nozzles. Each of the washes at these positions is optional. As in the prior embodiment, the nozzles may be oriented in a variety of ways in order to avoid dislodging the pellet of solid phase 114 collected at the respective magnet 116; the goal is to remove liquid phase, then refill, without disturbing the collected particles.

In FIG. 5A, a separation and wash process is illustrated wherein resuspension wash is not used. Typically, the assay will pass the resuspension wash position (position H in the figures) with the reaction vessel being filled with wash solution that was added either at position F or G. By providing "full width" magnets, or magnets which extend across the entire extent of the reaction vessel position, at positions G and I, any tendency to split the particle band to the left or right is reduced. Depending upon the response of a particular reagent mixture to magnetic field manipulation, this tendency may be evident with the trimmed magnets of the foregoing embodiment.

For instance, certain "sticky" mixtures react to the trimmed magnet at position G of FIG. 1A by accumulating on the left side of the cuvette wall most proximate the magnets (as viewed in FIG. 1A). This accumulation is maintained through position H. Then, with the trimmed magnet at position I, part of the magnetic particles break free of the previous accumulation and gather on the right side, while another part of the accumulation remains on the left side of the cuvette wall. Since the nozzle 136 which dispenses the final reagent at position P is preferably aimed at the middle of the cuvette wall most proximate the magnets, this split band of particles is not directly impinged by the final reagent stream, and incomplete resuspension is achieved.

However, in the embodiment of FIGS. 5A and 5B, full width magnets at positions G and I avoid this split-banding, and consequently result in more complete resuspension in the final reaction mixture at position P.

Without resuspension wash at position H, the reduced strength magnet at position H is strong enough to hold the previously collected particle band 114 and prevent the particles from being attracted to the stronger magnetic forces at the neighboring positions, positions G and I, which would otherwise result in split-banding.

The reduced strength magnet may be provided as a magnet having dimensions similar to that of the remaining magnets of the array but which provides a weaker magnetic field. Alternatively, it may be preferred to provide a magnet identical to the remaining magnets of the array, only disposed further from the respective reaction vessel position, such as by recessing the magnet, thus resulting in a weaker effective magnetic field at the cuvette. See FIG. 6 for an illustration of a recessed magnet at position H. Also, the material behind or around the magnet can be utilized to impact the effective magnetic field strength that acts on the particles to separate them from the solution and hold them to the cuvette wall during washing. Further, the reduced strength magnet may be implemented by recessing a single magnet of the same strength as all other magnets of the array, though all of the remaining reaction vessel positions employ two magnets of opposing polarity. Thus, in Figs. 5A and 5B, the magnet at position H appears to be half-height with respect to the magnet pairs of the remaining positions.

In FIG. 5B, the use of a resuspension wash in the instant configuration is illustrated. Here, wash fluid is aspirated out of the cuvette at position G but will not be replaced there. Rather, the cuvette is moved to the resuspension wash position, position H, without any liquid phase in the cuvette. The resuspension wash nozzle 133 is aimed at the particle aggregate on the "back" wall of the cuvette, most proximate the magnets. Since the magnetic forces holding the particles against the wall at this position are of reduced strength, the force of the resuspension wash stream is capable of resuspending much of the particle aggregation. However, the particles will immediately begin recollecting and will continue to do so at the stepped down magnet positions which follow (i.e., at positions I, J, K, . . . ). Any non-specific label that was trapped in the aggregate will now be freed into the wash solution and will be aspirated out of the reaction vessel at either wash position M and/or N.

In either case, the magnet array of FIGS. 5A and 5B typically provides a particle aggregation of consistent shape and position within the respective cuvette at the critical final resuspension position, position P, regardless of the characteristics of the contents of the assay mixture.

The tube 121 at position N of FIGS. 5A and 5B is employed to aspirate liquid phase from the respective cuvette 112 prior to the introduction, at position P, of the final reagent via the nozzle 136. This reagent facilitates the subsequent chemiluminescent reaction within a luminometer. The reagent dispensing nozzle 136 at position P is preferably angled towards the pellet 114 for maximum dispersion of the accumulated particles.

Figure 6:
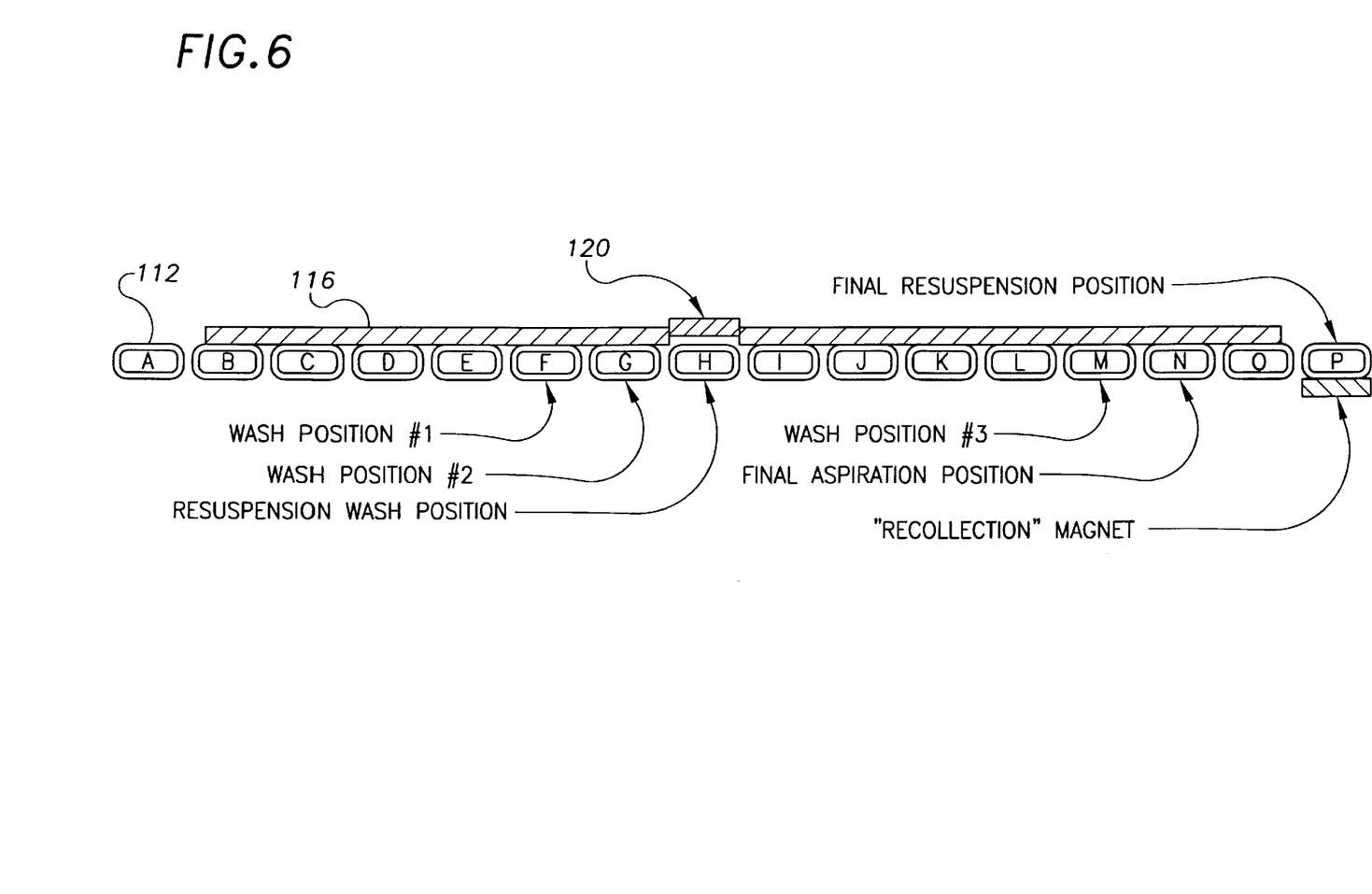
FIG. 6 is a top view of the magnet array of FIG. 5A.

In order to facilitate the complete dispersion of the pellet 114 in the stream of final reagent at position P, the respective magnet for that reaction vessel position, which may be referred to as a "recollection" magnet, is preferably positioned on the opposite side of the cuvette with respect to all other reaction vessel positions, as shown in the top view of FIG. 6. This "recollection" magnet is not shown in FIGS. 5A and 5B as it would otherwise obscure a portion of the cuvette 112 at position P. The purpose of positioning the magnet at this manner is to assist the stream of reagent in releasing the pellet from the wall of the cuvette and to aid in fully resuspending the magnetic particles in the final reagent mixture. The cuvette does not remain at position P long enough for the magnetic particles to begin re-accumulating proximate this final, oppositely positioned magnet to any significant degree. This is especially so since reagent is being introduced into the cuvette for most of the dwell time at this position.

In contrast to the system illustrated in FIGS. 1A and 1B, the magnets at reaction vessel position I and subsequent positions are disposed lower than the magnets at positions A through G. The magnets at the start of the separation (the initial separation stage) are positioned with respect to the height of the cuvettes to accommodate a wide range of initial reaction volumes. For example, if a high volume of liquid phase is present in a cuvette, the magnetic forces as provided by the embodiments of FIGS. 5A and 5B are sufficient to collect particles from the farthest distances in the reaction fluid both above and below the magnetic centerline. Once so collected, however, it is desirable to shift the particle aggregation lower within the cuvette so that the aggregate is positioned below the fluid level of the final resuspension fluid volume. The lower magnets after this step-down achieve the desired aggregate repositioning more completely than the previous embodiment for certain reaction mixtures. Since the resuspension wash volume does not participate in the final reaction, being withdrawn at the latest at position N, it can be selected such that the lower set of magnets is capable of recollecting all particles, including those in the upper portion of the resuspension wash volume.

Assay mixtures which resist repositioning of the particle mass tend to get even less responsive the longer they are maintained in one location. Thus, delaying the step-down to a later reaction vessel position within the subsequent separation stage, such as at position K in FIGS. 1A and 1B, only tends to make the aggregate more difficult to accurately position. Locating the step-down immediately following the resuspension wash position avoids this difficulty.

These and other examples of the invention illustrated above are intended by way of example and the actual scope of the invention is to be determined from the following claims.

What is claimed is:

1. A system, for use in an assay apparatus, for enabling separation and wash of magnetic particles in a reaction vessel, said magnetic particles having sample components bound thereto, the system comprising:

an array of plural, consecutive reaction vessel positions, each of said reaction vessel positions having a respective magnet adjacent thereto, past which said reaction vessel transits in sequence, said array comprising
an initial separation stage comprised of a first consecutive plurality of said reaction vessel positions,
a resuspension wash position comprised of one of said reaction vessel positions, adjacent said initial separation stage,
a subsequent separation stage comprised of a second consecutive plurality of said reaction vessel positions, adjacent said resuspension wash position,
a final aspiration position comprised of one of said reaction vessel positions, adjacent said subsequent separation stage, and
a final resuspension position comprised of one of said reaction vessel positions, adjacent said final aspiration position;

an initial aspiration element, adjacent a first of said reaction vessel positions of said initial separation stage, for selectively aspirating a quantity of liquid phase from said reaction vessel at said initial separation stage first reaction vessel position;

a resuspension wash dispense element, adjacent said resuspension wash position, for selectively dispensing resuspension wash buffer into said reaction vessel at said resuspension wash position;

a final aspiration element, adjacent said final aspiration position, for selectively aspirating a quantity of liquid phase from said reaction vessel at said final aspiration position; and a reagent dispense element, adjacent said final resuspension position, for selectively dispensing a reagent into said reaction vessel at said final resuspension position to resuspend said magnetic particles in said reagent, wherein said array is configured such that said reaction vessel transits, in sequential order, said initial separation stage, said resuspension wash position, said subsequent separation stage, said final aspiration position, and said final resuspension position, wherein said magnet adjacent said resuspension wash position is of reduced magnetic strength relative to all other magnets adjacent said array of plural consecutive reaction vessel positions.

2. The system of claim 1, wherein said magnets adjacent said initial separation stage, said subsequent separation stage, and said final aspiration position provide a magnetic field which attracts said magnetic particles into a substantially horizontal cluster on an interior wall of said reaction vessel most proximate said magnets.

3. The system of claim 2, wherein said magnets adjacent said subsequent separation stage and said final aspiration position are disposed such that said substantially horizontal cluster develops at a point, on said interior wall of said reaction vessel most proximate said magnets, below a point where said substantially horizontal cluster develops at said initial separation stage.

4. The system of claim 1, further comprising at least one rest position intermediate said final aspiration position and said final resuspension position past which said reaction vessel transits in sequence.

5. A method of separating and selectively washing magnetic particles within a reaction vessel, said magnetic particles having sample components bound thereto, the method comprising the steps of:

passing said reaction vessel through an array of reaction vessel positions of an assay apparatus, comprising an initial separation stage, a resuspension wash position, a subsequent separation stage, a final aspiration position, and a final resuspension position, for separating said magnetic particles from a liquid phase in said reaction vessel and washing said magnetic particles free of unbound sample components, wherein:

said initial separation stage comprised of a first consecutive plurality of said reaction vessel positions and an initial aspiration element, adjacent a first of said reaction vessel positions of said initial separation stage, for selectively aspirating a quantity of liquid phase from said reaction vessel at said initial separation stage first reaction vessel position;

said resuspension wash position comprised of one of said reaction vessel positions, adjacent said initial separation stage, and a resuspension wash dispense element, adjacent said resuspension wash position, for selectively dispensing resuspension wash buffer into said reaction vessel at said resuspension wash position;

said subsequent separation stage comprised of a second consecutive plurality of said reaction vessel positions, adjacent said resuspension wash position;

a final aspiration position comprised of one of said reaction vessel positions, adjacent said subsequent separation stage, and a final aspiration element, adjacent said final aspiration position, for selectively aspirating a quantity of liquid phase from said reaction vessel at said final aspiration position; and a final resuspension position comprised of one of said reaction vessel positions, adjacent said final aspiration position, and a reagent dispense element, adjacent said final resuspension position, for selectively dispensing a reagent into said reaction vessel at said final resuspension position to resuspend said magnetic particles in said reagent, wherein said array is configured such that said reaction vessel transits, in sequential order, said initial separation stage, said resuspension wash position, said subsequent separation stage, said final aspiration position, and said final resuspension position, and wherein said magnet adjacent said resuspension wash position is of reduced magnetic strength relative to all other magnets adjacent said array of plural consecutive reaction vessel positions.

* * * * *